United States Patent [19]

Fino

[11] Patent Number: 5,541,333
[45] Date of Patent: Jul. 30, 1996

[54] CARBAZOLE DERIVATIVES

[75] Inventor: James R. Fino, Antioch, Ill.

[73] Assignee: Abbott Laboratories, Abbott Park, Ill.

[21] Appl. No.: 421,334

[22] Filed: Apr. 13, 1995

Related U.S. Application Data

[60] Division of Ser. No. 84,495, Jul. 1, 1993, Pat. No. 5,464,746, which is a continuation-in-part of Ser. No. 808,839, Dec. 17, 1991, abandoned.

[51] Int. Cl.$^6$ .................................. C07F 9/24; C07F 9/40
[52] U.S. Cl. .................... 548/113; 548/444; 549/460; 549/461
[58] Field of Search .............................................. 548/113

[56] References Cited

U.S. PATENT DOCUMENTS

| | | | |
|---|---|---|---|
| 4,238,472 | 12/1980 | Albro et al. | 424/1 |
| 4,798,807 | 1/1989 | Vanderlaan et al. | 436/548 |
| 5,204,374 | 4/1993 | Muller et al. | 514/209 |

FOREIGN PATENT DOCUMENTS

| | | |
|---|---|---|
| 0204922 | 4/1986 | European Pat. Off. . |
| 0332819 | 1/1989 | European Pat. Off. . |
| 61-275655 | 12/1986 | Japan . |
| 2339396 | 2/1975 | United Kingdom . |

OTHER PUBLICATIONS

Binding of 7H–dibenzo[c,g]carbazole to polynucleotides and DNA in vitro Lindquist, et al vol. 10, No. 12, pp. 2187–2195, 1989.

Control of Prostaglandin–Induced Parturition in Sows by Injection of the β–Adrenergic Blocking Agent Carazolol and Oxytocin Holtz, et al *J. Anim. Sci.*, vol. 68, pp. 3967–3971, 1990.

Monoclonal Antibodies for Dioxin: Antibody Characterization and Assay Development Stanker, et al *Toxicology*, vol. 45, pp. 229–243, 1987.

Development of an Immunoassay for Chlorinated Dioxins Based on a Monoclonal Antibody and an Enzyme linked Immunosorbent Assay (Elisa) Stanker, et al *Chemosphere*, vol. 16, Nos. 8/9, pp. 1635–1639, 1987.

Photochemical linking of primary aromatic amines to carrier proteins to elicit antibody response against the amine haptens Pandey, et al *Journal of Immunological Methods*, vol. 94, pp. 237–246, 1986.

Chemical Abstracts Service: 114:178390 (1991).

Chemical Abstracts Service: 113:94368 (1990).

Chemical Abstracts Service: 107:20389 (1987).

Chemical Abstracts Service: 89:142890 (1978).

Chemical Abstracts Service: 89:171007 (1975).

*Primary Examiner*—Bernard Dentz
*Attorney, Agent, or Firm*—Paul D. Yasger; Thomas D. Brainard

[57] ABSTRACT

Novel tethered hapten intermediates and related conjugates based on carbazole and/or dibenzofuran, as well as methods for making and using such conjugates. Haptens based on the above core structures may be substituted at any position on the aromatic rings with a wide variety of substituents. Using tethered intermediates, immunogens, tracers, solid supports and labeled oligonucleotides are all described; as are methods for using the intermediates to prepare the conjugates, methods of using the conjugates to make and purify antibodies, as assay tracers, and in nucleic acid hybridization assays. Kits containing haptenated oligonucleotides and anti-hapten conjugates are also described.

5 Claims, No Drawings

CARBAZOLE DERIVATIVES

This application is a division of U.S. patent application Ser. No. 08/084,495, filed Jul. 1, 1993, now U.S. Pat. No. 5,464,746, which is a continuation-in-part of U.S. Ser. No. 07/808,839 filed Dec. 17, 1991, now abandoned the whole of which is incorporated by reference.

The present invention relates to novel carbazole and dibenzofuran hapten compounds, to tethered intermediates, to immunogens useful for preparing antibodies, to tracer compounds useful for assaying the haptens, to oligonucleotides labeled with the haptens and to kits containing these reagents. The invention also relates to various methods for making and/or using the novel haptens and the derivatives specified above.

I. BACKGROUND OF THE INVENTION

It is commonly known that many small molecules will not elicit an antibody response by themselves but, when coupled to an appropriate immunogenicity conferring carrier molecule (to become an immunogen), antibodies can be prepared against the hapten. This technology is discussed in many textbooks. See Erlanger, B. F. in *Methods of Enzymology*, 70:85–105 (Academic Press 1980); and Hum, B. A. L., et al., in *Methods of Enzymology*, 70:105- (Academic Press 1980).

Many methods of adding haptens to oligonucleotide probes are known in the literature. A review of such conjugate literature is found in Goodchild, *Bioconjugate Chemistry*, 1(3): 165–187 (1990). Enzo Biochemical (New York) and Clontech (Palo Alto) both have described and commercialized probe labeling techniques, including techniques for labeling probes with biotin or similar haptens. In addition, co-pending applications U.S. patent application Ser. Nos. 625,566, filed Dec. 11, 1990 now abandoned and 630,908, filed Dec. 20, 1990 now U.S. Pat. No. 5,290,925 teach methods for labeling probes at their 5" and 3" ends respectively. The entire disclosures of the aforementioned co-pending applications are incorporated by reference. The hapten label or "hook" may be used either to isolate a desired target sequence (i.e. by hybridization with a haptenated oligonucleotide and collection of the haptens with a specific binding partner); or to attach a detectable signaling moiety to a target sequence (e.g. by probing target with a haptenated oligonucleotide and using an anti-hapten conjugate with a detectable signal generating compound such as a fluorophore, chemilumiphore, colloidal particle or enzyme).

According to one known method for labeling an oligonucleotide, a label-phosphoramidite reagent is prepared and used to add the label to the oligonucleotide during its synthesis. For example, see Thuong, N. T. et al., *Tet. Letters*, 29(46):5905–5908 (1988); or Cohen, J. S. et al., U.S. patent application Ser. No. 07/246,688 now abandoned (NTIS ORDER No. PAT-APPL-7-246,688) (1989). However, DNA synthesis reaction conditions are quite severe (e.g. iodine oxidation and ammonium hydroxide cleavage) and many haptens (e.g. biotin and fluorescein) do not readily withstand these conditions without modification. In another approach useful for labile haptens, a linker having a protected terminal amine is attached to the desired end of the oligonucleotide. The amine can be deprotected and, under milder conditions, reacted with a label.

Automated synthesis of oligonucleotides (See e.g. Beaucage and Caruthers, *Tet. Letters*, 22(20):1859–1862 (1981) and U.S. Pat. Nos. 4,973,679 and 4,458,066) is often the most efficient method of preparing probes. However, the hostile conditions required during automated synthesis limit the choice of labels available for labeling by this method. The present invention overcomes these drawbacks by describing novel haptens which will withstand the rather rigorous conditions of DNA synthesis. Thus, using the haptens of the invention, an oligonucleotide can be directly labeled during automated synthesis, without involving an intervening isolation or a secondary labeling reaction.

The invention has a further advantage in that successfully labeled oligonucleotides can easily be isolated from unlabeled oligonucleotides by an affinity separation method using a specific binding partner, e.g. an antibody, for the hapten.

Methodology for preparing tracer molecules also is known. For example, fluorescence polarization assays require tracers comprising an analyte-hapten coupled to a fluorescent molecule. Typically, the analyte-hapten and a known amount of tracer are allowed to compete for a limited amount of a specific binding member for the hapten, and the labeled tracer is thereby partitioned between a bound and free form. The signal from the bound form is differentiable from the signal from the free form, so that the amount of analyte-hapten can be estimated. One method for differentiating the signals is by fluorescence polarization immunoassay (FPIA), in which the "millipolarization", the "span" or the "relative intensity" can be measured as described in the literature and below. The technique of FPIA has been described, for example, in Jolley, M. E., *J. Analyt. Toxicol.*, 5:236–240 (1981) and in Blecka, L. J. *Amer. Assoc. Clin. Chem.* pp. 1–6 (March 1983), the entire disclosures of which are incorporated herein by reference.

Some researchers have prepared antibodies to (i.e. demonstrated immunogenicity of) polyhalogenated dibenzofurans in the context of toxic byproduct detection and cleanup. For example, Vanderlaan, et al have worked with polyhalogenated p-dioxins (which differ from dibenzofuran in having a six-member, 2 oxygen spacer ring between the two benzene rings, instead of a 5 member, one oxygen furan) and polyhalogenated dibenzofurans; see e.g. U.S. Pat. No. 4,798,807, EP-A-332 819, *Chemosphere*, 16(8–9): 1635–39 (1987), *Toxicology*, 45(3):229–43 (1987). U.S. Pat. No. 4,238,472 to Albro, et al., describes antibodies to and immunogens made from similar polychlorinated compounds. Albro, et al. show that antisera to the polychlorinated dioxins and dibenzofurans had very little reactivity with the unchlorinated species.

Pandey, et al., *J. Immunol. Methods*, 94(1–2):237–46 (1986), describe antibodies to and immunogens made from 3-azido-N-ethylcarbazole.

However, applicants are unaware of any an demonstrating the antigenicity or immunogenicity of the claimed carbazole and dibenzofuran derivatives.

II. SUMMARY OF THE PRESENT INVENTION

In one aspect, the present invention is derived from the class of compounds which are based carbazole and dibenzofuran derivatives of the following structure:

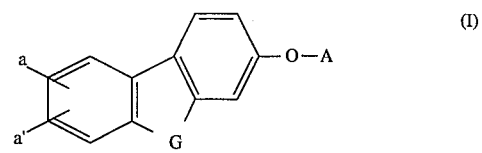

wherein a and a' when taken alone are 1 to 4 groups independently selected from the group consisting of: hydrogen, $C_1-C_{10}$-alkyl, $C_1-C_{10}$-alkoxy, $C_1-C_{10}$-alkylthio, halo-$C_1-C_{10}$-alkyl, $C_1-C_{10}$-alkylamino, di-($C_1-C_{10}$-alkyl)amino, aryl $C_1-C_{10}$-alkyl, optionally substituted aryl, halogen, amino, carboxy, carboxamido, hydroxy, mercapto, nitro, nitroso, sulfo, phospho and protected forms thereof; or alternatively a and a' when adjacent and when taken together with the carbons to which they are joined form a fused ring;

G is selected from S,O and NR wherein R is hydrogen, $C_1-C_{10}$-alkyl, optionally substituted aryl, optionally substituted sulfonyl, thiophenyl, carboxy, carboxamido, and protected forms thereof; and A is a linking moiety of the formula -L-y, wherein y is a functional group that can react directly or after activation with functional groups in a second molecule and L is spacer group consisting of from 1 to about 50 atoms.

In another aspect, the present invention relates to conjugate compounds having the following structure:

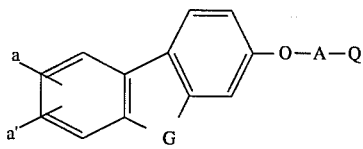

(II)

wherein a and a', G and A are as defined above; and

Q is an immunogenicity conferring carrier molecule, a detectable label, an oligonucleotide or a solid support.

In another aspect, the invention relates to antibodies, either polyclonal or monoclonal, which are reactive with the above compounds (I) or (II). Such antibodies may be prepared by the process of injecting an immunogen (II) into an animal and recovering the antibodies.

In addition, the invention relates to the following methods of using the above compounds:

1. Use of compounds (II) to prepare immunogens, tracers, labeled oligonucleotides and affinity solid supports;
2. Use of compounds (III: Q=immunogenicity conferring carrier) to raise antibodies;
3. Use of compounds (III: Q=solid support) to isolate or purify antibodies;
4. Use of compounds (III: Q=oligonucleotide) for detection of nucleic acids complementary to the oligonucleotide; and
5. Use of compounds (III: Q=detectable signal moiety) for detection of hapten-analog analytes.

Finally, the invention also relates to kits containing compounds of the invention (e.g. II:y=phosphoramidite or III: Q=oligonucleotide), in combination with an antibody reactive with the compounds, said antibody being attached to or adapted for attachment to either solid supports or detectable labels. In the second example, the oligonucleotide probe may be hybridized with a target and the antibody may be used to separate or detect it. In the first example, the phosphoramidite may be used to label one's own oligonucleotide during its synthesis, while the antibody is used as before.

III. DETAILED DESCRIPTION

The following definitions are applicable to the present invention:

"Antigen" is defined in its usual sense, to refer to a molecule or compound which is capable of eliciting an immune or antibody response in a challenged animal.

Compounds which are not antigenic by themselves can sometimes by made to elicit the immune response by coupling the compound (a "hapten") to an "immunogenicity conferring carrier" molecule to form an "immunogen". While such haptens are not "antigenic" in the strict sense, they are capable of imitating antigens and have many properties in common with antigens. Thus, the terms antigen and hapten are often used interchangeably. For example, both haptens and antigens have at least one "determinant" which, as used herein, refers to a region of the antigen or hapten which is involved in specific binding reactions between the antigen or hapten and an antibody. Some haptens and antigens have more than one determinant region or site and thus are "polyvalent". In essence, it is the determinants which differentiate antigens, and therefore, antibodies from one another on the basis of immunological specificity.

For purposes of this application, "hapten" is defined as any compound having the core structure shown below:

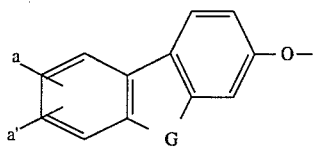

(I)

wherein a and a' when taken alone are 1 to 4 groups independently selected from the group consisting of: hydrogen, $C_1-C_{10}$-alkyl, $C_1-C_{10}$-alkoxy, $C_1-C_{10}$-alkylthio, halo-$C_1-C_{10}$-alkyl, $C_1-C_{10}$-alkylamino, di-($C_1-C_{10}$-alkyl)amino, aryl-$C_1-C_{10}$-alkyl, optionally substituted aryl, halogen, amino, carboxy, carboxamido, hydroxy, mercapto, nitro, nitroso, sulfo, phospho and protected forms thereof; or alternatively a and a' when adjacent and when taken together with the carbons to which they are joined form a fused ring;

G is selected from S, O, and NR wherein R is hydrogen, $C_1-C_{10}$-alkyl, optionally substituted aryl, optionally substituted sulfonyl, thiophenyl, carboxy, carboxamido, and protected forms thereof.

As suggested above, the term "immunogen" refers to a conjugate of a hapten or antigen and a carrier molecule. The carrier is often a protein or peptide. Known immunogenicity conferring carriers include, for example, naturally occurring poly(amino-acids), albumins and serum proteins such as bovine thyroglobulin (BTG), globulins, lipoproteins, ocular lens proteins, bovine serum albumin (BSA), keyhole limpet hemocyanin (KLH), egg ovalbumin, bovine gamma globulin (BGG), thyroxin binding globulin (TBG), and the like. Alternatively, synthetic poly(amino-acids) can be utilized such as polylysine, etc. However, any molecule which is capable of conferring antigenicity to a hapten is an "immunogenicity conferring carrier."

The term "hapten-specific binding member", as used herein, refers to a member, such as an antibody or receptor, that specifically binds to the hapten. The determinants on the hapten are responsible for the specific binding of the binding member to the hapten. The most common and usual specific binding member is an antibody, either polyclonal or monoclonal.

In general, terms like "alkyl", "alkenyl" and "aryl" have the meanings usually attributed to them by persons skilled in the art of organic chemistry. For example, alkyl refers to monovalent straight or branched aliphatic radicals which may be derived from alkanes by the removal of one hydrogen, and have the general formula $C_nH_{2n+1}$. Alkyl substituents may have from 1 to about 30 carbons, more practically 1 to about 20. "Lower alkyl" refers to alkyls having from 1 to about 10 carbons. Examples of lower alkyl include CH₃—, CH₃CH₂—, CH₃CH(CH₃)—, and CH₃(CH₂)₄—.

"Alkylene" refers to a divalent group derived from a straight or branched chain saturated hydrocarbon by removal of two hydrogen atoms. Examples include methylene, 1,2-ethylene, 1,3-propylene, 2,2-dimethylpropylene and the like.

"Halo-$C_1$-$C_{10}$-alkyl" refers to a lower alkyl group, as defined below, bearing at least one halogen substituent, for example chloromethyl, fluoromethyl, chloroethyl, trifluoromethyl and the like.

"$C_1$-$C_{10}$-alkoxy" refers to an alkyl group, as defined above, which is bonded through an oxygen atom. Examples of such alkoxy groups include methoxy, ethoxy, t-butoxy and the like.

"$C_1$-$C_{10}$-alkylamino" refers to amino groups substituted with one or two lower alkyl groups, as defined above, including methylamino, ethylamino, dimethylamino, diethylamino, propylamino and ethylmethylamino.

"$C_1$-$C_{10}$-alkylthio" refers to thio groups substituted with one or two lower alkyl groups, as defined above, including methylthio, ethylthio, dimethylthio, and diethylthio.

"Alkenyl" refers to monovalent straight or branched aliphatic radicals which may be derived from alkenes by the removal of one hydrogen, and have the general formula $C_nH_{2n-1}$. Alkenyl substituents may have from 1 to about 30 carbons, more practically 1 to about 20. "Lower alkenyl" refers to alkenyls having from 1 to about 10 carbons. "Olefinic" is a synonym for alkenyl.

"Aryl" refers to a monovalent radical derived from aromatic hydrocarbons or heteroaromatic compounds by the removal of one hydrogen. Aryl substituents have ring structures, such as those of phenyl, naphthyl and 2-thienyl. Typically, aryl substituents are planar with the π electron clouds of each carbon remaining on opposite sides of the plane. Aryl substituents satisfy the Huckel (4n+2) π electrons rule.

"Arylalkyl" refers to an aryl group as defined above substitute with one to two lower alkyl groups as defined above.

Protecting groups are defined as groups that can be removed under specific conditions, but which shelter or hide a reactive atom or functionality temporarily during intermediate reactions under other conditions. Protecting groups for hydroxyl, amino and thiol functionalities are well known in the art (T. W. Greene, Protective Groups in Organic Synthesis, John Wiley and Sons, NY, 1981). Hydroxyl functions are routinely protected as alkyl or aryl ethers alkyl, aryl, alkenyl), silyl ethers (silyl), esters (acyl), carbonates (C(=O)—O—alkyl, —C(=O)—O—aryl, —C(=O)—O—alkenyl) and carbamates (C(=O)—NH-alkyl, —C(=O)—NH-aryl, —C(=O)—NH-alkenyl). Amino functions are routinely protected as carbamates (—C(=O)—O—alkyl, —C(=O)—O—aryl,(C(=O)—O—alkenyl), amides (C(=O)—alkyl, —C(=O)—aryl, —C(=O)—alkenyl), cyclic imides (phthaloyl), N-benzyl derivatives (—CH$_{(n)}$aryl$_{(3-n)}$, n=1–3), imine derivatives (=CH$_{(n)}$alkyl$_{(2-n)}$, =CH$_{(n)}$aryl$_{(2-n)}$ n=0–2), silyl derivatives (silyl), N-sulfenyl derivatives (S-aryl, —S—CH$_{(n)}$aryl$_{(3-n)}$, n=0–3), and N-sulfonyl derivatives (—SO₂-aryl, —SO₂-alkyl). Thiol functions are routinely protected as thioethers (—CH$_{(n)}$aryl$_{(3-n)}$, n=1–3, alkyl), thioesters (acyl), thiocarbonates (C(=O)—O—alkyl, —C(=O)—O—aryl, —C(=O)—O—alkenyl), thiocarbamates (C(=O)—NH-alkyl, —C(=O)—NH-aryl, —C(=O)—NH-alkenyl), and disulfides (—S—alkyl, aryl). Where more than one protecting group is called for, it will be understood that each group may be independently selected from the various protecting groups. Indeed, one of ordinary skill in the art will know which protecting groups are routine for which functional groups.

As used herein, the "linking moiety" A is also referred to as a "tether". These terms refer to the spacer molecule having the formula:

—L—y where y is a reactive functional group that can react directly or after activation with the functional groups in a second molecule, e.g. the conjugation partner, Q; and L is a spacer group consisting of from 1 to 50 carbon and heteroatoms. Typically, L will include not more than ten heteroatoms, and will be arranged in a straight or branched chain or cyclic moiety, saturated or unsaturated, with the provisos that not more than two heteroatoms may be directly linked in the sequence —L—y, that the sequence —L—y cannot contain —O—O— linkages, that cyclic moieties contain 6 or fewer members, and that branchings may occur only on carbon atoms. In formulas where A is already linked to Q, the group y is dropped from the formula, leaving A =—L—.

Typically, y is chosen from the group consisting of hydroxy (—OH), thiol (—SH), carboxy (—C(=O)OH), amino (—NH₂), aldehyde (—CH(=O)), leaving group, Michael acceptor, phosphoramidite, phosphonate and protected forms of these functional groups. In synthesis, the linking moiety often comprises a bifunctional compound designated x—L—y wherein x is also a functional group (selected from the same group as y) which can react with functional groups on the hapten or —R. Many bifunctional linkers are known to one skilled in this art. For example, heterobifunctional linkers are described in, e.g. U.S. Pat. No. 5,002,883 (Bieniarz). These are preferred in some cases due to the specificity of their ends for one functional group or another.

A "Michael acceptor" is defined in the art as follows: "The nucleophilic addition of enolate (or analogous) anions to the carbon-carbon double bond of α,β-unsaturated ketones, aldehydes nitriles or carboxylic acid derivatives, [is] a process known as the Michael reaction . . . The unsaturated compounds in the reaction, often called Michael acceptors, may include any unsaturated system having a functional group capable of stabilizing the carbanionic intermediate . . . . The Michael acceptors may also add a variety of nucleophiles such as alcohols, thios, and amines." H. O. House, Modern Synthetic Reactions, W. A. Benjamin, Inc., Menlo Park Calif, 1972, pp. 595-96. Common functional groups which can activate a double bond to this kind of nucleophilic addition (thereby forming Michael acceptors) include, —CH(=O), —C(=O)R†, —C(=O)NH₂, —CN, —NO₂, —S(=O)R†, —S(=O)₂R†, wherein R†, can be alkyl or aryl. Thus, exemplary Michael acceptors include:

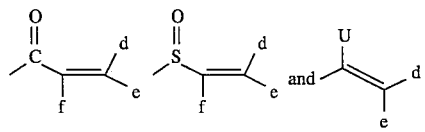

wherein d, e, and f can independently be hydrogen, alkyl, or aryl, and wherein U is chosen from —CH(=O), —C(=O)R†, —C(=O)NH₂, —CN, —NO₂, —S(=O)R†, and —S(=O)₂R†, and R†is again alkyl or aryl. A particularly preferred Michael acceptor is maleimide:

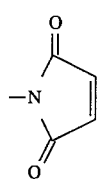

Solid supports refer to a wide variety of support materials. Polymeric plastics, such as polystyrene, polypropylene, and polytetrafluoroethylene, are exemplary. Glass is also a useful support. Supports may take any size or shape, including beads, microparticles, tubes, rods, plates, wells and cuvettes. Supports may include functional groups for conjugation, or may be derivatized prior to conjugation. Alternatively, supports may be coated or adsorbed in some cases. Supports should be physically separable from reagent solutions, based on size, weight, shape, charge, magnetic properties or some other physical property. It will be realized that two distinct uses for solid supports are described herein. First, antibodies can be purified using supports conjugated to tethered intermediates; and secondly, supports to which anti-hapten antibodies are attached are useful for separating and/or detecting oligonucleotides labeled with haptens, and for competitive hapten-analog assays.

Antibodies are prepared by developing an immune response in animals to the immunogens described hereinafter. The immunogen is administered to animals such as rabbits, mice, rats, sheep or cows by a series of injections according to techniques generally known in the art. An antibody, according to the present invention, is raised in response to an immunogen of the invention which is derived from the haptens described above. Both polyclonal and monoclonal antibodies recognize specific epitopes on an immunogen, and, while typically polyclonal antibodies have been utilized in the present invention, both may be suitable. Polyclonal antibodies consist of a mixture of multiple antibodies, each recognizing a specific epitope, some of which may be present on the carrier molecule. Techniques for preparing polyclonal antibodies generally are well known in the art. It is well within the skill of the ordinary practitioner to isolate antibodies which are specific for the hapten portion of the immunogen. Affinity chromatography is but one method.

Monoclonal antibodies, specific for just one determinant or epitope, may be prepared eliciting an immune response as before. Following appropriate incubation and booster injections, B-lymphocyte cells are removed from the spleens of the animals by standard procedures, and the B-lymphocyte cells are then fused with myeloma fusion partners according to standard procedures, such as those described in Kohler and Milstein, "Continuous Culture of Fused Cells Secreting Antibody of Predefined Specificity," *Nature*, 256, 495 (1975).

"Label" as used herein refers to labels capable of providing a directly detectable signal, as well as to molecules like haptens, which can indirectly be detected. In this way, "label" is interchangeable with "reporter" or "hook". However, at times is necessary to distinguish "label" from a moiety which is capable of generating a measurable detectable signal, usually an electromagnetic radiation signal. The term "detectable label" or "signaling" label or moiety is used when the intent is to differentiate from hapten-type labels or "hooks".

The term "tracer" refers to a conjugate of hapten with a detectable signaling label. The tracer permits a determination or assay of the amount of hapten present in an unknown solution. Preferably, the tracer signaling label is a fluorescent molecule as described hereinafter, although the tracer signaling label may encompass other detectable labels, including by way of example and not limitation, radioisotopes, chemilumiphores and colloidal particles. In an FPIA, the choice of the fluorescent molecule for forming the tracer is advantageously flexible and is largely up to the preferences of the practitioner. It will be readily appreciated that the fluorescent labels are ideally chosen in accordance with their size, that is, the smaller the molecule, the more rapidly it can rotate, and the more effective it is as an FPIA tracer component. In the present invention, the preferred fluorescent labels are fluorescein and fluorescein derivatives. These compounds provide fluorescent response when excited by polarized light of an appropriate wavelength and thereby enable the fluorescence polarization measurement. For example, any of the following fluorescein derivatives can be used: fluorescein amine, carboxyfluorescein, a-iodoacetamidofluorescein, 4'-aminomethylfluorescein, 4'-N-alkylaminomethylfluorescein, 5-aminomethylfluorescein, 2,4-dichloro-1,3,5-triazin-2-yl-aminofluorescein (DTAF), 4-chloro-6-methoxy-1,3,5-triazin-2-yl-aminofluorescein, fluorescein isothiocyanate. Especially preferred derivatives are aminomethylfluorescein and 5-carboxyfluorescein. Other tracer detectable labels are also known in the literature, particularly associated with other detection techniques.

The term "oligonucleotide" (sometimes abbreviated to "oligo") refers to short segments of nucleic acid having a minimum of about 5 nucleotides and a maximum of several hundred nucleotides. Although, oligonucleotides longer than about 30 nucleotides are often called polynucleotides, the term oligonucleotide is used herein to encompass the longer chains as well. The nucleic acid may be RNA or DNA, although DNA is generally preferred. The DNA may be natural or synthetic, although the invention excels in the automated synthesis of DNA.

Reagents

1 Haptens a. Structure of Haptens

Haptens which are structurally similar to carbazole or dibenzofuran have the following general structure:

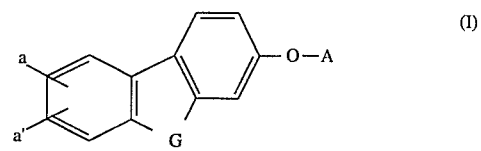

wherein G is O (dibenzofuran) or NR (carbazole), a, a', and A are as defined above.

b. Synthesis of Haptens

Hapten derivatives may be prepared according to routine chemistry using carbazole and dibenzofuran core structures commercially available. The examples provide further details on synthesis.

Also, it will be recognized by one of normal skill in the an that there are some limitations for the substituents a and a' when adjacent and taken together to form a fused ring. The ring fused to the phenyl will normally have from 4–10 atoms, and preferably from 6–8 atoms.

c. Tethered intermediates

The haptens are converted according to methods known to those skilled in the art using linker molecules x—L—y, (containing reactive functional groups x and y capable of coupling to complementary reactive groups on another molecule or macromolecule) to produce hapten intermediate compounds with a tether or side chain, —L—y. Of course, the remainder of the hapten molecule retains a structure substantially similar to those of the desired determinant(s). Many methods for linking a hapten to another molecule are known in the art. Preferred methods involve activating a functional group on the hapten or linker, and attaching a linker or tether to the hapten via the activated group. The free end of the tether, y, is available for coupling to the desired conjugate molecule, Q. As is known in the art, it is sometimes desirable to activate a functional group on Q, and sometimes a second linker is used. Depending on the desired y group, it may also be preferred (for ease of synthesis) to interchange one y for another (e.g. phosphoramidite or phosphonate for hydroxyl) after the tether has been attached to the hapten.

One possible general activation/coupling scheme is given below. Specific examples follow for various means for preparing desired products.

The hapten (I) with a hydroxyl group is reacted with an activated linker or tether molecule x—L—y, wherein x is a leaving group; wherein L is spacer group as defined above; and wherein y is chosen from the group consisting of hydroxy, carboxy and amino to form a tethered intermediate (II). For example, the hapten hydroxyl may be reacted in base with ethyl 4-bromobutyrate (where x=Br, L=—$(CH_2)_3$— and y=$CO_2C_2H_5$). The tether, —L—y thus becomes —$O(CH_2)_3$—$CO_2C_2H_5$). The ethyl ester may be deprotected to a carboxylic acid by saponification. The carboxylic acid is a reactive group capable of reacting with functional groups in the conjugate partner Q. The reaction conditions for each of these reaction steps can be obtained from specific examples in the EXAMPLES section or in the literature.

2 Immunogens a. Structure of Immunogens

Immunogens can be produced from a wide variety of tethered intermediates. The immunogens of the present invention have the following general structure:

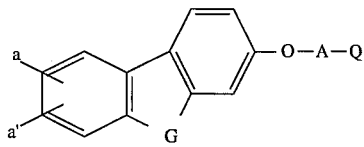
(II)

wherein a and a', G and A are as defined above; and Q is an immunogenicity conferring carrier molecule, a detectable label, an oligonucleotide or a solid support.

Typical carriers were previously described. Immunogens find principal use in the raising of antibodies.

b. Synthesis of Immunogens

In the immunogens of the present invention, the tether functionality, y, of tethered intermediates (II) can be reacted in any of several ways known to those skilled in the art with the amino groups on a protein carrier. With carboxyl reactive groups, it is frequently preferable to form amide bonds, which typically are quite stable. Amide bonds are formed by first activating the carboxyl moiety y of the tethered intermediate by reaction with an activating reagent such as 1,3-dicyclohexylcarbodiimide and an additive such as N-hydroxysuccinimide. The activated form of the hapten is then reacted with a buffered solution containing the immunogenicity conferring carrier. Alternatively, the carboxylic acid hapten may be converted, with or without isolation, into a highly reactive mixed anhydride, acyl halide, acyl imidazolide, or mixed carbonate and then combined with the immunogenicity conferring carrier. One of ordinary skill in the art will recognize that there are many reagents that can be used to form amide bonds other than those listed.

A tethered intermediate with a terminal amine functionality [II, y=—$NH_2$] can be transformed into a highly reactive N-hydroxysuccinimide urethane by reaction with N,N'-disuccinimidyl carbonate in a suitable solvent, such as acetonitrile or dimethylformamide. The resultant urethane is then reacted with the immunogenicity conferring carrier in a buffered, aqueous solution to provide an immunogen.

A tethered intermediate with a terminal aldehyde functionality [II, y=—CH(=O)] can be coupled to the immunogenicity conferring carrier in a buffered, aqueous solution and in the presence of sodium cyanoborohydride, by reductive amination according the methods known to those skilled in the art.

Alternatively, tethered intermediates containing an alcohol group [II, y=—OH] can be coupled to the immunogenicity conferring carrier by first reaction it with phosgene or a phosgene equivalent, such as di or triphosgene or carbonyldiimidazole, resulting in the formation of a highly reactive chloroformate or imidazoloformate derivative (usually without isolation). The resultant active formate ester is then reacted with the immunogenicity conferring carrier in a buffered, aqueous solution to provide an immunogen.

In a manner analogous to immunogens, tethered intermediates can be conjugated to solid supports having functional groups such as amino, hydroxyl or carboxyl groups that are reactive in a complementary sense with reactive groups, y on the linker of the intermediate. The result is a solid phase which can be used to separate or purify antibodies against the hapten.

2 Antibodies

Methods for antibody preparation are generally known and have been summarized above. Specific examples using the haptens and immunogens of the present invention are given in the example section below.

3 Tracers a. Structure of Tracers

Tracers of the present invention look very much like the immunogens described above, except that Q is a signaling moiety. Tracers have the general structure as described above.

As mentioned above, detectable labels which can be detected in homogeneous systems are preferred. Particularly preferred are fluorescein and fluorescein derivatives.

Tracers of the invention find use in assays for carbazole and dibenzofuran derivatives, including oligonucleotides derivatized with this hapten. For tracers of the present invention it is preferred that the linker consist of 1 to 12 carbon and heteroatoms. Longer chains reduce the differential polarization effects by distancing the label from the high molecular weight molecule that modulates its polarization properties.

b. Synthesis of Tracers

Tethered intermediates (II) containing an amino group, a carboxyl group or an alcohol group in the tether can be coupled to fluorescein or a fluorescein derivative to prepare the tracers of the present invention. Tethered intermediates with a terminal amine functionality can be transformed into a highly reactive N-hydroxysuccinimide urethane by reaction with N,N'-disuccinimidyl carbonate in a suitable solvent, such as acetonitrile or dimethylformamide. Or an amine-terminated tethered intermediate can be activated to an isocyanate. The resultant product is then reacted with an amino fluorescein derivative to form a urea tracer. An amino-group-containing hapten can also be coupled to a carboxyfluorescein derivative which has been activated with N-hydroxysuccinimide in a suitable solvent.

Tethered intermediates with a terminal carboxyl group on the linker can be coupled to an amino-terminal fluorescein derivative by first activating the carboxylic acid moiety of the tether by reaction with an activating reagent such as 1,3-dicyclohexylcarbodiimide and an additive such as N-hydroxysuccinimide. The activated intermediate is then reacted with a solution of the fluorescein derivative, resulting in the formation of a tracer. Alternatively, the carboxylic acid hapten may be converted, with or without isolation, into a highly reactive mixed anhydride, acyl halide, acyl imidazolide, or mixed carbonate and then combined with the fluorescein derivative.

Alternatively, tethered intermediates containing an alcohol group can be coupled to the fluorescein by first reacting the tethered intermediate with phosgene or a phosgene equivalent, such as di or triphosgene or carbonyldiimidazole, resulting in the formation of a highly reactive chloroformate or imidazoloformate derivative (usually without isolation). The resultant active formate ester is then reacted with an amino-terminal fluorescein derivative resulting the formation of a tracer.

4 Oligonucleotides a. Structure of Oligonucleotides

Oligonucleotides can be produced from a wide variety of tethered intermediates.

As noted below, oligonucleotides labeled with haptens find uses in nucleic acid hybridization assays, including amplification assays. Haptenated oligonucleotide probes are well adapted for separation and/or detection of PCR products (see e.g. EP-A-357 011) and/or LCR products (see e.g. EP-A-439 182). In combination with other haptens, (e.g. biotin, fluorescein, dansyl, acetylaminofluorene and iodoacetylaminofluorene, etc.) probes labeled with the hapten of this invention are particularly useful in multiplex versions of PCR and LCR.

b. Synthesis of Tethered Oligonucleotides

In the oligonucleotides of the present invention, the tether functionality y, can be the same as defined above for tracers and immunogens. Oligonucleotides can be labeled by reacting the y functionality with an amino or hydroxyl function of the oligonucleotide, or by direct reaction with the phosphorous via oxidative amination of an H-phosphonate reagent. Amino functionalities are present in the purine and pyrimidine bases, but these sites are less preferred for labeling because of their importance in hybridization. Amino functionalities can be introduced to the 5' and/or 3' ends of oligonucleotides using reagents such as Aminomodifier® (Clontech, Palo Alto). Hydroxyl functions are typically formed during automated synthesis.

A preferred method for adding a hapten to the 3' end of an oligonucleotide is disclosed in co-pending, co-owned U.S. patent application Ser. No. 630,908, filed Dec. 20, 1990, the disclosure of which has already been incorporated. A preferred method for adding a hapten to the 5' end is through the use of a phosphoramidite reagent as described in Thuong, et al. or Cohen, et al. cited above in the Background Section.

For example a tethered hapten intermediate (II, y=phosphoramidite) where the phosphoramidite, y, is

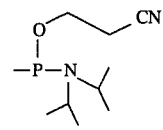

is prepared from the tethered hapten (II, y=—OH) by reaction with N,N-diisopropyl-O-(2-cyanoethyl)chlorophosphoramidite as described in Scheme I, below.

The starting compound in Scheme I is an ester of general formula 1 wherein W is a spacer group of from 1 to about 50 atoms arranged in a straight or branched chain or cyclic moiety, saturated or unsaturated, with the provisos that (a) not more than two heteroatoms are directly linked, (b) cyclic moieties contain 6 or fewer members, and (c) branching occurs only on carbon atoms; $R^1$ and $R^{10}$ are independently hydrogen, alkyl of from 1–10 carbon atoms, an amino protecting group, or aryl, alternatively $R^1$ or $R^{10}$ when taken together with W and the nitrogen atom to which they are attached may form a cyclic amine. Compound 1 undergoes base hydrolysis in the presence of glyme (step 1), followed by reaction with Meldrum's acid (2,2-dimethyl-1,3-dioxane-4,6-dione, 2) and $R^2OH$ ($R^2$ is alkyl of from 1–6 carbon atoms) to yield the beta-ketoester 3 which is then reduced (step 4) with a borohydride at low temperature, e.g., 15°–30° C. for 23–24 hours and neutralized slowly to the diol 4. The neutralization must be done very slowly to avoid a dangerously fast release of gas. The primary hydroxyl of the diol is then protected by dimethoxytritylation (step 5) to form the tethered hapten 5. The tethered hapten is then phosphoramidated at the secondary alcohol (step 6) to the phosporamidite-linked hapten 6. The phosphoramidite-linked hapten may then be used directly to introduce the hapten into a synthetic oligonucleotide at any position.

Scheme 1
Prpearation of Phosphoramidite-linked Hapten

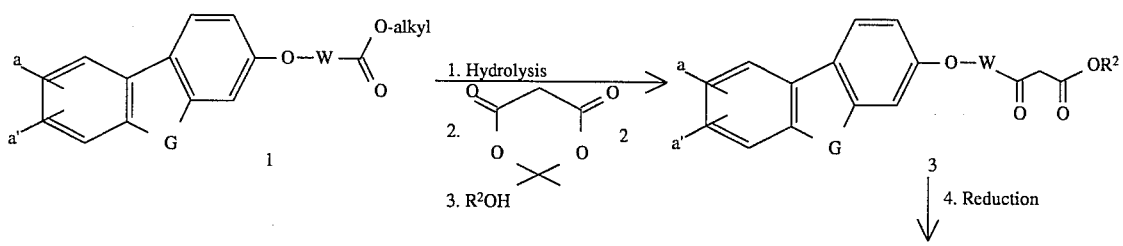

-continued
Scheme 1
Prpearation of Phosphoramidite-linked Hapten

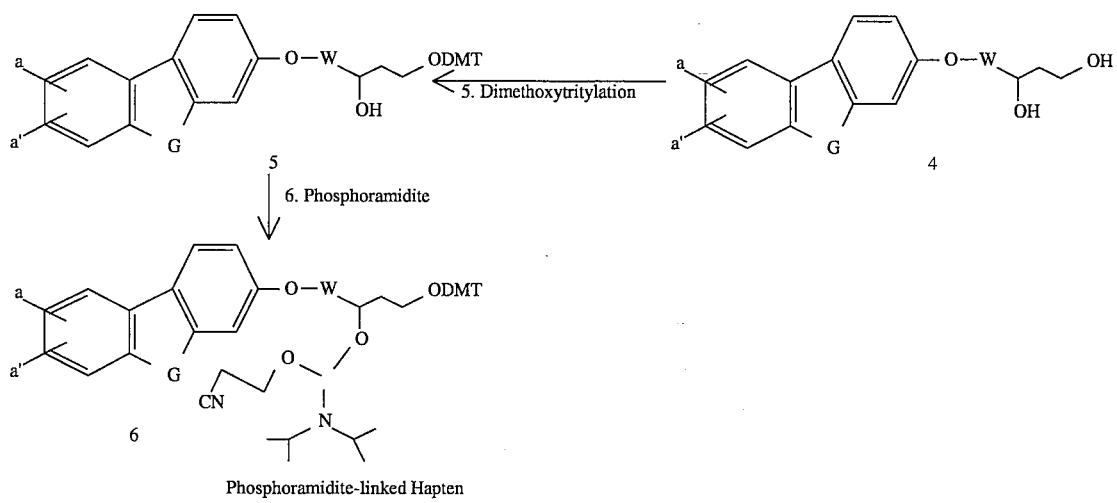

Phosphoramidite-linked Hapten

Alternatively, a tethered hapten intermediate (II, y=phosphonate) where the phosphonate is is prepared from the tethered hapten (II, y=—OH] by reaction with phosphorous trichloride followed by hydrolysis. Both the phosphoramidite and phosphonate derivatives are readily incorporated into oligonucleotides during synthesis using standard protocols.

Alternatively, a tethered hapten (II, y=—NH$_2$] is reacted in the presence of carbon tetrachloride with a phosphonate group already incorporated in to the oligonucleotide, via oxidative amidation.

Detailed descriptions of procedures for solid phase synthesis of oligonucleotides are widely available, e.g., U.S. Pat. Nos. 4,401,796 and 4,458,066 which are incorporated by reference. In one embodiment of the present invention synthesis of hapten-labeled oligonucleotides is accomplished by reacting a hapten phosphoramidite with the 5' hydroxyl of a nucleotide attached to a growing oligonucleotide chain. The labeled oligonucleotides are purified by standard procedures, e.g., Gait, *Oligonucleotide Synthesis: A Practical Approach* (IRL Press, Washington, D.C.: 1984).

Of course, it is now fairly routine practice to make oligonucleotides by synthetic methods in automated synthesizers that are commercially available, for example Applied Biosystem's DNA Synthesizer 380B.

B. FPIA Assay Methods

The tracers and antibodies raised against immunogens of the present invention produce excellent results in a fluorescence polarization assay of the present invention for the semi-quantitative detection of hapten derivatives. The assay is performed in accordance with the general procedure of Example 27.

The preferred procedure was designed to be conducted on the TDx® Therapeutic Drug Monitoring System or the ADx™ Abused Drug System, IMx® Fluorescence Polarization and Microparticle Enzyme Immunoassay (MEIA) Analyzer all of which are available from Abbott Laboratories, Abbott Park, Ill. When the TDx, ADx, or IMx systems are used, the assays are fully automated from pretreatment to final reading once the test sample has been prepared. Manual assays, however, can also be performed. Although the principles of the invention are applicable to manual assays, the automated nature of the TDx, ADx and IMx systems assures minimal technician time to perform assays and interpret data. The results can be quantified in terms of "millipolarization units", "span" (in millipolarization units) and "relative intensity". The measurement of millipolarization units indicates the maximum polarization when a maximum amount of the tracer is bound to the antibody in the absence of any PCB in the test sample. The higher the net millipolarization units, the better the binding of the tracer to the antibody.

The span is an indication of the difference between the net millipolarization and the minimum amount of tracer bound to the antibody. A larger span provides for a better numerical analysis of the data. For the purposes of the present invention, a span of at least 15 millipolarization units is preferred.

The intensity is a measure of the strength of the fluorescence signal above the background fluorescence. Thus, a higher intensity will give a more accurate measurement. The intensity is determined as the sum of the vertically polarized intensity plus twice the horizontally polarized intensity. The intensity can range from a signal of about three times to about thirty times the background noise, depending upon the concentration of the tracer and other assay variables. For the purposes of the present invention, an intensity of about three to about twenty times that of background noise is preferred, although it is within the skill of the routineer to optimize the signal for each particular system.

For fluorescein tracers, the pH at which the method of the present invention is practiced must be sufficient to allow the fluorescein moiety to exist in its open form. The pH can range from about four to nine, preferably from about six to eight, and most preferably from about 7 to 7.5. Various buffers can be used to achieve and maintain the pH during the assay procedure. Representative buffers include borate, phosphate, carbonate, Tris, barbital and the like. The particular buffer used is not critical to be present invention, but the Tris and phosphate buffers are preferred.

The preferred FPIA procedure is especially designed to be used in conjunction with the Abbott TDx® Clinical Analyzer, the Abbott TDxFLx™ or the Abbott ADx® Drugs of Abuse System, all three of which are available from Abbott Laboratories, Abbott Park, Ill. The calibrators, controls, or unknown samples are piperted directly into the sample well of the TDx® sample cartridge. One of the advantages of this procedure is that the sample does not require any special preparation. The assay procedure from this point is fully automated.

If a manual assay is being performed, the sample is mixed with the pretreatment solution in dilution buffer and a background reading is taken. The fluorescence tracer is then mixed with the assay. The antibody is then finally mixed into the test solution. After incubation, a fluorescence polarization reading is taken.

The fluorescence polarization value of each calibrator, control or sample is determined and is printed on the output tape of an instrument, such as the Abbott TDx® Analyzer, TDxFLx™ or ADx® System. A standard curve is generated in the instrument by plotting the polarization of each calibrator versus its concentration using a nonlinear regression analysis. The concentration of each control or sample is read off of the stored calibration curve and printed on the output tape.

With respect to the foregoing preferred procedure, it should be noted that the tracer, antibody, pretreatment solution, wash solution, calibrators and controls should be stored between about 2 degrees C and about 8 degrees C while the dilution buffer should be stored at ambient temperature. A standard curve and controls should be run every two weeks, with each calibrator and control run in duplicate. All samples can be run in duplicate.

The preferred reagents, calibrators and controls for a preferred fluorescence polarization immunoassay of the present invention can be found in the Example Section, infra.

C. Methods of Use

Methods of using the novel haptens, tethered intermediates, immunogens, solid supports and tracers have each been described above. Methods of using the labeled oligonucleotides include the performance of specific hybridizations, such as sandwich hybridizations known in the art. For example, see U.S. Pat. No. 4,486,539 (Ranki) and GB 2 169 403 (Orion). The haptenated oligonucleotides may also be used in amplification techniques, such as PCR and LCR. An illustrative use of a haptenated primer in PCR is described in EP-A-357 011 (Abbott); the use of a haptenated probe in LCR is described in EP-A-320 308 and in EP-A-0 439 182. Each of the above-mentioned disclosures is incorporated herein by reference.

The invention will now be described by way of examples which are intended to illustrate but not limit the invention.

IV. EXAMPLES

All percentages expressed herein are weight/volume unless otherwise indicated. Unless stated otherwise, the following abbreviations have the meanings given, and all chemical reagents are from Aldrich Chemical, (Milwaukee, WI).

| | |
|---|---|
| ACA | aminocaproic acid |
| AMF or AMF | aminomethyl fluorescein, a fluorophore (Abbott) |
| BAE | 3 carboxypropyloxy radical Butyric Acid Ester |
| BSA | Bovine Serum Albumin, an immunogenicity conferring carrier. (Sigma Chemical) |
| Celite ® | A trademark of Manville Products Corporation, for diatomaceous earth |
| CDI | 1,1' carbonyldiimidazole, a coupling reagent |
| DCC | dicyclohexylcarbodiimide |
| DEAD or DEADC | diethylazodicarboxylate |
| DIEA | diisopropylethylamine |
| DMAP | 4-(N,N-dimethylamino)pyridine |
| DMEM | Dulbecco's Minimum Essential Medium, a cell culture medium. |
| DMF | N,N-dimethylformamide |
| EBB | ethyl 4-bromobutyrate |
| EEDQ | 2-ethoxy-1-ethoxycarbonyl-1,2-dihydroquinoline |
| glyme | 1,2-dimethoxyethane |
| HNQ | 8-hydroxy-5-nitroquinoline |
| HOSu or NHS | N-hydroxysuccinimide |
| KLH | keyhole limpet hemocyanin, an immunogenicity conferring carrier (CalBioChem) |
| NMP | N-methylpyrrolidinone |
| PEG | polyethylene glycol |
| TBAF | tetrabutylammonium fluoride |
| TEA | triethylamine |
| THF | tetrahydrofuran |

A. Synthesis of intermediates, Tethers, and Tethered Haptens

Example 1: 2-[3-Carboxypropyloxy]-carbazole ethyl ester (G33), a tethered hapten.

2-Hydroxycarbazole (5.0 g, 27 mmol), ethyl bromobutyrate (EBB, 5.9 mL, 41 mmol), and potassium carbonate (5.7 g, 41 mmol) were refluxed in methylethyl ketone (50 mL) for 18 h. Tetrahydrofuran (60 mL) was added to the reaction and it was filtered. The solvent removed under reduced pressure and the solid triturated with hexanes to remove excess EBB. The yield was 8.1 grams of a light tan solid after drying under reduced pressure. Mass spectrum: DCI/NH$_3$, (m+H)+@m/z 298, (m+NH$_4$)+@m/z 315.

Example 2: 2-[3-Carboxypropyloxy]-carbazole (Carbazole-BAE, G40), a tethered hapten.

Carbazole ester (1.0 g), prepared above, was dissolved in glyme (30 mL) and aqueous lithium hydroxide (7 mL, 0.5N). After stirring for 24 h at ambient temperature, the solvent was removed under reduced temperature and water (10 mL) was added. The solution was acidified to pH 2.0 with aqueous HC(1N) then extracted with ethyl acetate. The organic extract was dried and the solvent removed under reduced pressure giving a colored solid (0.82 g). Mass spectrum: DCI/NH$_3$, (m+H)+@m/z 270, (m+NH$_4$)+@m/z 287.

Example 3: Active ester of carbazole derivative (G57), a tethered hapten.

Carbazole-BAE (0.1 g, 0.37 mmol), prepared above (G40), and N-hydroxysuccinimide (0.051 g, 0.45 mmol) were dissolved in NMP (1 mL) then DCC (0.084 g, 0.41 mmol) was added. The reaction was stirred at ambient temperature for 18 h then filtered through Celite and diluted to 2 mL with NMP. This solution of active ester was used in later examples below.

Example 4: 2-[3-Carboxypropyloxy]-N-[2-thiophenylsulfonyl]-carbazole (CT, H39), a tethered hapten.

Carbazole ester (2.0 g, 6.7 mmol) prepared above (G33) was dissolved in tetrahydrofuran (THF, 20 mL) and the solution cooled in an ice bath. To the cooled solution, under N$_2$ atmosphere, was added sodium hydride (0.225 g, 80%, 74 mmol) and the reaction allowed to come to ambient temperature then heated at 40° C. for 6h. The reaction was cooled in an ice bath and a solution of thiophenesulfonyl chloride (1.22 g, 6.7 mmol) in THF (20 mL) was added dropwise over 5 minutes. The reaction was allowed to come to ambient temperature then heated at 40° C for 18 h, under N₂, protected from light. The solvent was removed under reduced pressure and the residue taken up in glyme (60 mL) and aqueous lithium hydroxide (15 mL, 0.5N). After 18 h at ambient temperature the solvent was removed under reduced pressure and water (20 mL) was added. The solution was acidified to pH 2.0 with aqueous HCl (1N) and the solution extracted with ethyl acetate. The organic solution was dried with sodium sulfate and the solvent removed under reduced pressure giving the product as a colored solid. Mass spec: DCI/NH₃; (m+NH₄)+@m/z 433, (m+NH₄-H₂O)+@m/z 415.

Example 5: Active ester of carbazole-thiophene derivative (G58), a tethered hapten.

CT (0.2 g, 0.48 mmol), prepared above (H39), and N-hydroxysuccinimide (0.066 g, 0.58 mmol) were dissolved in NMP (1 mL) and then DCC (0.11 g, 0.53 mmol) was added. The reaction was stirred under nitrogen atmosphere for 18 h then filtered through Celite. The solution was diluted to 2.5 mL with NMP. The active ester solution was used in later examples.

Example 6: 2-[3-t-Butyldimethylsilyloxypropyloxy]-dibenzofuran (Dbf-silyl ether, F141), a tethered hapten.

2-Hydroxydibenzofuran (3.0 gm, 16.3 mmol), t-butyldimethylsilyl-propanediol (3.1 gm, 16.3 mmol), and triphenylphosphine (5.1 gm, 19.5 mmol) were dissolved in tetrahydrofuran (30 mL). The solution was cooled in an ice bath under N₂ atmosphere and then diethylazodicarboxylate 3.8 mL, 19.5 mmol) was added slowly. The reaction was stirred at room temperature for 18 h then the solvent was removed under reduced pressure. The residue was purified by column chromatography (silica gel, 1:9, ethyl acetate/hexanes). Mass spectrum: DCI/NH₃, (m+H)+@m/z 357, (m+NH₄)+@m/z 374.

Example 7: 2-[3-hydroxypropyloxy]-dibenzofuran (Dbf-alcohoi, F145), a tethered hapten.

The Dbf-silyl ether (1.0 gm, 2.8 mmol) prepared above (F141) was taken up in dry tetrahydrofuran (2 mL) and TBAF (5.6 mL, 1.0 M in THF, 5.6 mmol). The reaction was stirred at ambient temperature for 30 min. then the solvent was removed under reduced pressure. The residue was dissolved in ethyl acetate (40 mL), washed with water (3×12 mL), and saturated brine (12 mL). The solution was dried over anhydrous. sodium sulfate and the solvent removed under reduced pressure giving a very pure product. Mass spectrum: DCI/NH₃, (m+H)+@m/z 243, (m+NH₄)+@m/z 260, (m+NH₄.NH₃)+@m/z 277.

Example 8: 2-[3-carboxypropyloxy]-dibenzofuran (Dbf-BAE, F246), a tethered hapten.

2-Hydroxydibenzofuran (0.5 gm, 2.7 mmol), ethylbromobutyrate (0.78 mL, 5.4 mmol), potassium carbonate (1.1 gm, 8.1 mmol), and sodium iodide (10 mg) were combined in 2-butanone (15 mL). The reaction was refluxed until complete, then the reaction filtered and the solvent removed under reduced pressure. The residue was taken up in 6M aqueous KOH/methanol, 1:1. After the hydrolysis was complete the reaction was acidified to pH 3 and the product extracted with ethyl acetate. The residue was purified by column chromatography (silica gel, ethyl acetate/hexanes/ acetic acid, 10:30:60:0.5). The yield was 0.52 gm of product. Mass spectrum: DCI/NH₃, (m+H)+@m/z 271, (m+NH₄)+@m/z 288, (m+NH₄.NH₃)+@m/z 305.

Example 9: An imidizolide derivative of dibenzofuran (F146a), a tethered hapten.

Dbf-alcohol (0.275 g, 1.1 mmol), prepared above (F145) was dissolved in NMP (1.5 mL) and then CDI (0.202 g, 1.2 mmol) was added. This provided the Dbf-alcohol imidizolide (shown below ) which was used as is in later examples.

Example 10: 12 Atom Tethered Carbazole Intermediate, a tethered hapten.

N-t-BOC-O-(2-aminoethyl)-2-aminoethanol hydrochloride (0.30 g, 1.25 mmol, prepared from 2-(2-aminoethoxy-)ethanol by the method of Mattingly, P. G., Synthesis (4):366–68, 1990), Carbazole-BAE (0.335 g, 1.25 mmol), and BOP reagent (0.551 g, 1.25 mmol) were dissolved in acetonitrile (5 mL), along with triethylamine (0.521 mL, 3.74 mmol), tetrahydrofuran (3 mL), and N-methylpyrrolidinone (2 mL). The reaction was kept at ambient temperature for 18 h under inert atmosphere. The solvent was removed in vacuo and the residue purified by column chromatography using ethyl acetate/hexanes as the eluant. Mass spectrum: DCI/NH₃, (m+H)+@m/z 456. The BOC protecting group was removed with trifluoroacetic acid/ dichloromethane (5 mL, 1:1) giving the trifluoroacetate salt of the amine.

Example 11: Carbazole Betaketoester, a tethered hapten.

The title compound is prepared according to Scheme 1, steps 1–3, above. The bold-faced compound numbers refer to the compounds in that scheme.

2-Hydroxycarbazole (25 g, 136 mmol), ethyl 4-bromobutyrate (29.3 mL, 205 mmol), potassium carbonate (28.3 g, 205 mmol), and sodium iodide (1 g) were refluxed in 2-butanone (250 mL), with vigorous stirring for 48 h. While the reaction was still warm, methylene chloride (750 mL) was added. The solution was filtered and the solvent removed in vacuo. The residue was washed with hexanes (1 L) with stirring for 30 min then filtered. The solid was dried in vacuo giving 38 g of solid. Hydrolysis is done in fresh glyme (35 mL/gram) using aqueous lithium hydroxide (0.5N, 2–4 equivalents). The basic solution is reduced in volume, in vacuo, water added, and brought to pH2 with aqueous HCl (1–6N). The product (1) is isolated either by filtration of the solid or by extraction with ethyl acetate.

In a 2 L round-bottom flask, 2-carboxypropyloxy-carbazole (1, 50.0 g, 186 mmole) was suspended in dry dichloromethane (700 mL) then Meldrum's acid (28 g, 195 mmole), diethyl cyanophosphonate (30 mL, 195 mmole) and triethylamine (52 mL, 371 mmole) were added along with additional dichloromethane (300 mL). The reaction was stirred for 25 hours at ambient temperature under dry nitrogen atmosphere. The solvent was removed in vacuo and the residue taken up in ethyl acetate (1300 mL). To this solution was added 500 mL of 1.0M phosphoric acid. After vigorous stirring for 30 minutes the precipitate was isolated and washed with water (7×200 mL). The solid was dissolved in methanol (1.4 L) and the solution heated to reflux for 5 hours. The solvent was remove in vacuo and the solid triturated in the presence of t-butylmethyl ether. The solid was isolated and washed with t-butylmethyl ether (200 mL) then dried in vacuo giving a tan colored solid (48 g, 3).

Example 12: Carbazole-diol, a tethered hapten.

The title compound is prepared according to Scheme 1, step 4 above. The bold-faced compound numbers refer to the compounds in that scheme.

Carbazole betaketo ester (3, prepared above, 47 g, 144 mmole) was dissolved in tetrahydrofuran (500 mL) then lithium borohydride (2M in tetrahydrofuran, 238 mL, 477 mmole) was added slowly using a cannula with stirring and under a dry inert atmosphere. After 24 hours, 10% citric acid (500 mL) was added very slowly. The solution was extracted with ethyl acetate (3×400 mL) and the combined organic extracts washed with 5% sodium bicarbonate (400 mL) and then concentrated brine (400 mL). The solution was dried over anhydrous sodium sulfate, filtered, and the solvent removed in vacuo giving a white solid (29 g). To purify the diol, it can be taken up in a large amount (2 L) of methanol and then the solvent removed in vacuo. This is repeated 4–6 times and then the solid (4) is dried in vacuo.

Example 13: Carbazole-diol-DMT, a tethered hapten.

The title compound is prepared according to Scheme 1, step 5 above. The bold-faced compound numbers refer to the compounds in that scheme.

Carbazole-diol (4, prepared above, 7.75 g, 25.9 mmole) was dissolved in dry pyridine (70 mL) and then dimethoxytrityl chloride (8.8 g, 25.9 mmole), diisopropylethylamine (4.5 mL, 33.7 mmole), and N,N-dimethylaminopyridine (0.16 g, 1.3 mmole) were added. The reaction was stirred under nitrogen atmosphere, protected from light, for 18 h at ambient temperature. The solvent was removed in vacuo and the residue purified by flash chromatography ( 6×22 cm bed of silica gel, ethyl acetate/hexanes/TEA: 0:100:1, 500 mL; 20:80:1, 1L; 40:60:1, to end). After removing solvent, residual TEA was removed by coevaporation with toluene and then methylene chloride giving 12.2 grams (>78%) of the title compound (5).

Example 14: Carbazole phosphoramidite, a tethered hapten.

The title compound is prepared according to Scheme 1, step 6 above. The bold-faced compound numbers refer to the compounds in that scheme.

The dry carbazole-diol-DMT (5, 6.0 g, 10 mmole) was dissolved in dry methylene chloride (80 mL) then diisopropylethylamine (7 mL, 40 mmole, distilled from CaH) and 2-cyanoethyl N,N-diisopropylchlorophosphoramidite (3.1 mL, 14 mmole) were added. The reaction was kept at ambient temperature, under nitrogen atmosphere, protected from light for 2 h. Dry methanol (0.6 mL) was added and then after 20 min ethyl acetate (200 mL) and TEA (50 mL) were added. The reaction was extracted with 10% sodium carbonate (2×200mL) and saturated brine (2×200mL), dried over sodium sulfate and the solvent removed in vacuo. The residue was purified by flash chromatography (3.2×50 cm bed of silica gel, ethyl acetate/hexanes/TEA: 0:100:1, 250 mL to condition column before applying sample; elution with 0:100:1, 250 mL; 20:80:1, 500 mL; 30:70:1, to end). Residual TEA was coevaporated with toluene then ethyl acetate/methylene chloride, 1:1, giving 6.05 g (76%) of white solid (6).

B. Synthesis of Immunogens

Example 15: Carbazole/BSA Immunogen (G59):

BSA (0.5 g) was dissolved in sodium phosphate buffer (pH8.0, 0.05M, 10 mL) then NMP (5 mL) was added. Carbazole active ester solution from the example above (G57)(1.7 mL) was added and the reaction mixed by rotation for 4 h at ambient temperature. The pH was adjusted with triethylamine (TEA, 0.5 mL) plus aqueous HCl (2 mL, 1.0N). Mixing was continued for a total of 18 h then the solution was dialyzed against 10% ethanol in sodium phosphate buffer (pH8.0, 0.1M, 3×6.6 L), then against distilled water (3×6L). The solution was lyophilized giving the immunogen as a white fluffy material (0.51 g)

Example 16: Carbazole-thiophene/BSA Immunogen (G60):

BSA (0.5 g) was dissolved in sodium phosphate buffer (10 mL, pH8.0, 0.05M) then NMP (5 mL) was added. To this solution was added CT-BAE active ester solution (1.6 mL) from example 5 (G58). The reaction was mixed by rotation, then after 2 h TEA (0.5 mL) was added followed by aqueous HCl (2 mL, 1N). After 18 h at ambient temperature, the solution was dialyzed against 10% ethanol in sodium phosphate buffer (pH8.0, 0.1M, 3×6.6 L), and distilled water (3×6 L). The solution was lyophilized, giving a fluffy, white product (0.52 g).

Example 17: Dibenzofuran/BSA Immunogen (G49):

Dbf-BAE (0.085 g, 0.3 mmol) prepared above (F246) and HOSu (0.054 g, 0.47 mmol) were dissolved in NMP (2 mL). To this solution was added DCC (0.084 g, 0.41 mmol) and the reaction stirred at ambient temperature for 18 h under $N_2$ atmosphere. BSA (0.5 g) was dissolved in sodium phosphate buffer (pH8.0, 0.05M) then NMP 2.3 mL) was added. The active ester solution was filtered and added to the protein solution. The reaction was mixed by rotation for 18 h at ambient temperature. The cloudy solution was dialyzed against sodium phosphate buffer (pH8.0. 0.1M) with 10% ethanol (3×6.6 L) at ambient temperature, then with distilled water (3×6 L) at 2°–8° C. Lyopholization gave the immunogen as a white powder (0.47 g).

Example 18: Dibenzofuran/KLH Immunogen (F147):

KLH (0.25 g) was dissolved in phosphate buffer (pH8.0, 10 mL) and then NMP (4 mL) was added. To this solution was added an aliquot of imidazolide (0.45 mL, 0.19 mmol), prepared above (F146a). After one hour additional imidizolide (0.30 mL, 0.13 mmol) was added. The reaction was stirred at ambient temperature for 18 h then dialyzed three times against ethanol/pH8.0 phosphate buffer (1:3, 4 L, 4 times). The solution was partially lyophilized then allowed to thaw. The solid was washed with water and lyopholized giving a grayish solid.

C. Synthesis of Tracers

Example 19: General Tracer Synthetic Procedures

A. General procedure I: A hapten (e.g. 25 mg) is activated with dicyclohexylcarbodiimide (0.07 mmol) and N-hydroxysuccinimide (NHS, 0.2 mmol) in tetrahydrofuran (5 mL, freshly distilled from benzophenone ketyl) or dimethyl formamide (5 mL) at 0° C. for 2 h and at ambient temperature for about 12 h under a nitrogen atmosphere. To an aliquot (1 mL) of the activated hapten is added an amino bearing fluorescein derivative (e.g. 4 mg) along with 2 drops of triethylamine. The reaction mixture is stirred for 12 h, evaporated and chromatographed [e.g. Whatman PLKC18F, 1 mm, 20×20 cm reverse phase plates, methanol/1% aq. acetic acid, 60:40 or MERCK Silica Gel 60 F-254, 2 mm, 20×20 cm, chloroform/methanol, 85:15].

B. General procedure II: A hapten (e.g. 25 mg) is dissolved in thionyl chloride (1 mL) and heated to 60° C. for 12 h. Afterwards the excess thionyl chloride is removed in vacuo, leaving the acid chloride of the hapten. The acid chloride is then dissolved in THF (5 mL, freshly distilled from benzophenone ketyl). To an aliquot (1 mL) of the activated hapten is added an amino bearing fluorescein derivative (e.g. 4 mg) along with 2 drops of triethylamine. The reaction mixture is stirred for 12 h, evaporated and chromatographed [e.g. Whatman PLKC18F, 1 mm, 20×20 cm reverse phase plates, methanol/1% aq. acetic acid, 60:40 or MERCK Silica Gel 60 F-254, 2 mm, 20×20 cm, chloroform/methanol, 85:15].

C. General procedure III: An amino bearing hapten is converted to its hydrochloride by treatment with ethereal hydrogen chloride. The hapten hydrochloride (e.g. 50 mg) is dissolved in THF (10 mL, freshly distilled from benzophenone ketyl) and treated with trichloromethyl chloroformate (100 mL) for 30 min under a nitrogen atmosphere. Afterwards the volatiles are removed in vacuo and the residue is taken up in DMF, divided into aliquots and treated with an amino bearing fluorescein derivative (e.g. 4 mg) along with one drop of triethylamine. After stirring for 12 h, the reaction mixture is evaporated and chromatographed [e.g. Whatman PLKC18F, 1 mm, 20×20 cm reverse phase plates, methanol/ 1% aq. acetic acid, 60:40 or MERCK Silica Gel 60 F-254, 2 mm, 20×20 cm, chloroform/methanol, 85:15].

Example 20: Carbazole/Aminomethylfluorescein Tracer (G61):

The remainder of the active ester solution prepared above (G57) was divided in two and to one part was added a small amount of 5-AMF and a drop of DIEA. After 72 h at ambient temperature, protected from light, the reaction was purified using preparative TLC (reverse phase, C18, 1000 μm plates, methanol/500 mM NaCl, 6:4) giving a tracer with the following structure:

The remainder of the active ester solution (G58) was divided in two and to one part was added a small amount of 5-AMF and a drop of DIEA. After 72h at ambient temperature, protected from light, the reaction was purified using preparative TLC (reverse phase, C18, 1000 μm plates, methanol/500 mM NaCl 6:4) giving the tracer shown below:

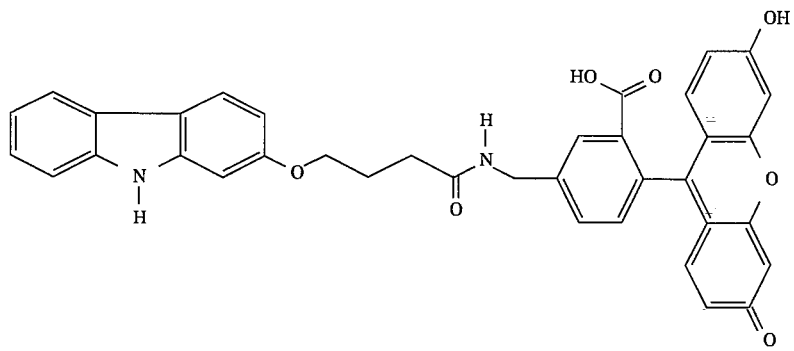

Mass spectrum: FAB, mH+@613.

Example 21: Carbazole/N-glycyfluoresceinamine Tracer

To a similar portion of active ester solution prepared above (G57) is added a small amount of N-glycylfluoresceinamine and a drop of DIEA. After about 72 h at ambient temperature, protected from light, the reaction is purified using preparative TLC (reverse phase, C18, 1000 μm plates, methanol/500 mM NaCl, 6:4) giving a tracer with the following structure:

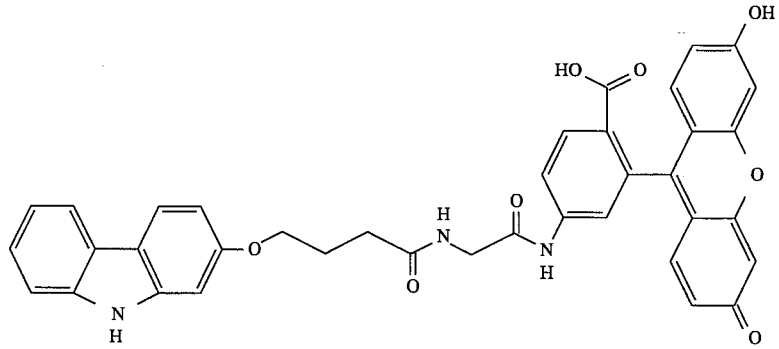

Example 22: Carbazole-thiophene/Aminomethyfluorescein Tracer (G62):

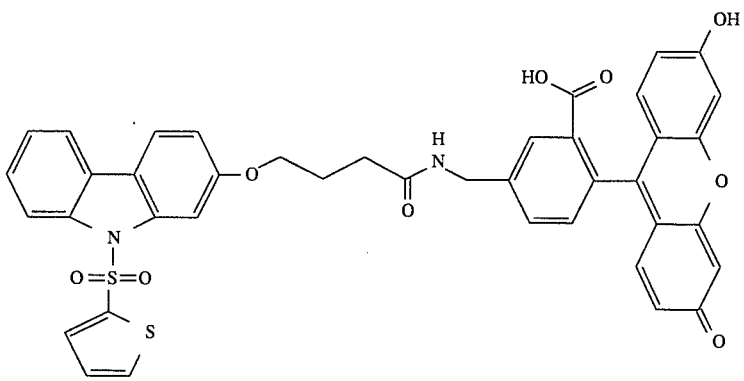

Mass spectrum: FAB mH+@759.

Example 23: Carbazole-thiophene/N-glycylfluoresceinamine Tracer:

To a similar portion of the active ester solution prepared above (G58) is added a small amount of N-glycylfluoresceinamine and a drop of DIEA. After about 72 h at ambient temperature, protected from light, the reaction is purified using preparative TLC (reverse phase, C18, 1000 μm plates, methanol/500 mM NaCl, 6:4) giving the tracer shown below:

An aliquot of the imidizolide (0.6 mL, 0.25 mmol), prepared above (F146a), was mixed with AMF.HCl (0.05 g, 0.13 mmol). After 18 h at ambient temperature the residue was purified by preparative TLC (silica gel, 2×2 mm plates, methanol/methylene chloride, 1:9), giving the tracer shown below.

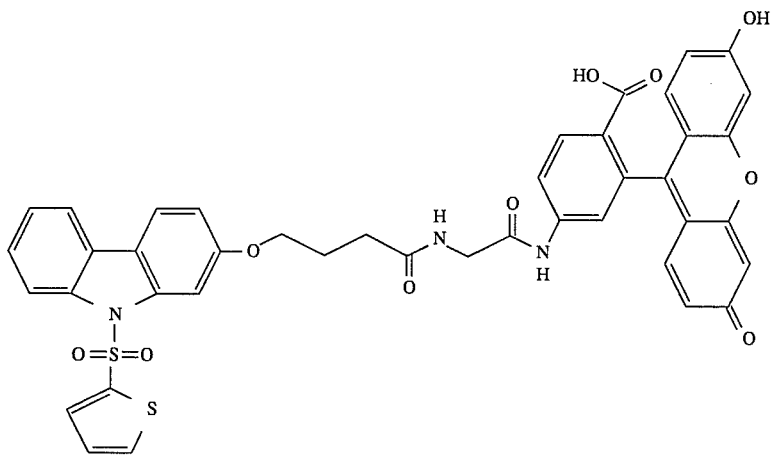

Example 24: Dibenzofuran/Aminomethyfluorescein Tracer (F146b):

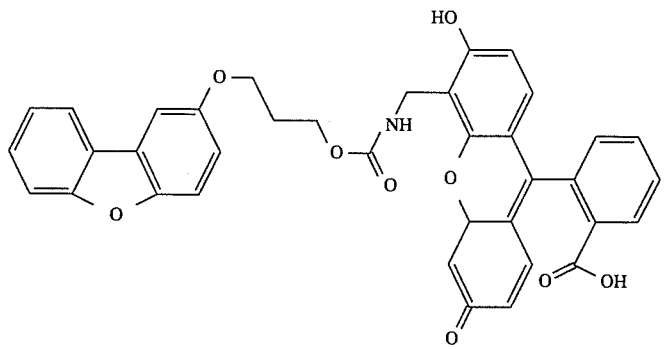

Mass spectrum: FAB, mH+@m/z 630

Example 25: Dibenzofuran/N-glycyfluoresceinamine Tracer

Dbf-BAE (0.022 mmol), prepared above (F246), and EEDQ (0.024 mmol) are dissolved in NMP (0.3 mL). After 2 h of stirring at ambient temperature, N-glycylfluoresceinamine (0.022 mmol) and DIEA (0.012 mL, 0.067 mmol) are added as in examples 17 and 19 above. After about 18 h at ambient temperature, protected from light, the solvent is removed under reduced pressure and the residue purified by preparative TLC (reversed phase C18, 1 mm, methanol/500 mM NaCL, 6:4) giving the tracer shown below.

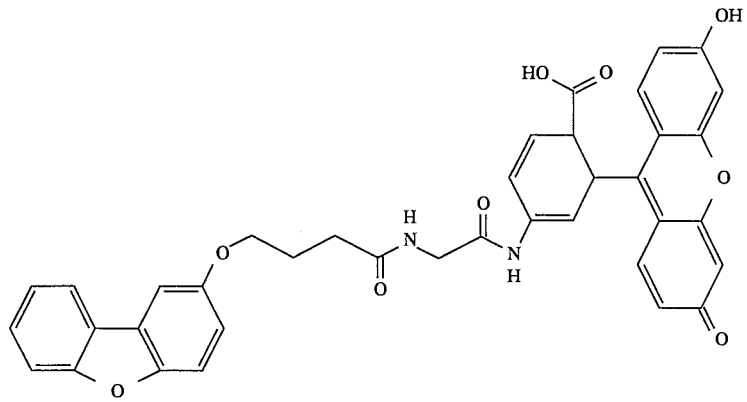

D. Production of Antisera

Example 26

Approximately four to five month old female New Zealand White rabbits were injected subcutaneously and intramuscularly with an initial inoculation of 0.2 mg of the immunogen in Freund's Complete Adjuvant followed by a day 14 boost of 0.1 mg of the immunogen and thereafter monthly booster injections of 0.05 mg in Freund's Incomplete Adjuvant. Bleeds were taken two weeks following each booster injection and the serum tested for binding to tracers in the TDx instrument. Antibodies with adequate net millipolarization and span were shown in some bleeds 6 weeks from initial inoculation.

E. Production of Hybridomas

Example 27

Four to six week old female BALB/c mice are injected subcutaneously at four weeks intervals with 0.2 mL of any of the immunogens prepared above ( e.g. 5 mg/mL; 0.06 mL of immunogen) in 1.88 mL saline; with 100 mg of monophosphoryl lipid A and trehalose dimycloate adjuvant (Ribi Immunochem Research, Inc). Three months from initial inoculation, upon testing positive for antibody activity, the donor mice are killed three days following the last immunization; the spleen is removed aseptically and placed in a plastic Petri dish with 5 mL of cold Dulbecco's Minimal Essential Medium (DMEM),with 2.0 mM L-glutamine (Medium A ). The spleen is dissociated into a single cell suspension; the cells are centrifuged to a pellet and the red cells lysed by resuspension in 2 mL of 0.83% ammonium chloride in 10 mM Tris buffer. After letting stand for 2 min., 20–30 mL of fresh medium A is added. The cells are washed by centrifugation and resuspended in 10 mL of fresh medium A.

An immunoglobulin non-secreting mouse myeloma cell line (SP 2/0) deficient in the enzyme hypoxanthine-guanine phosphoribosyl transferase (HGPRT-, EC2.4.2.8), as disclosed by Kearney, *Journal of Immunology*, 1979, 123, 1548, which is incorporated herein by reference, is used as the fusion partner. The myeloma cell line is maintained in medium A with 20% fetal calf serum added. For three days prior to fusion, 0.1 mM 8-azaguanine is added to the myeloma cells in order to kill any HGPRT+revertants. On the day of fusion, the myeloma cells are harvested, washed once in medium A, and resuspended in 5 mL medium A. The myeloma and previously harvested spleen cells are counted using a hemacytometer and their viability assessed by Erythrosin B stain exclusion.

The fusion technique used is modified from that of Gefter el. at., *Somatic Cell Genetics*, 1977, 3, 231, which is hereby incorporated by reference. To a sterile 50 mL conical centrifuge tube is added $1–1.5 \times 10^8$ spleen cells with an equal number of SP 2/0 myeloma cells. The myeloma-spleen cell suspension is centrifuged at 1400 rpm for 5 minutes to pellet the cells together. The supernatant is aspirated off and the tube tapped gently to loosen the cell pellet and 1 mL of 50% polyethylene glycol (PEG, MW 1000, Sigma) in DMEM, without serum, is added to the cell pellet. The cells are resuspended gently in PEG solution over a period of 1 minute by slowly aspirating up and down using a 1 mL pipette. The tube is held in the hand for an additional 1 minute and then 1 mL of medium A is added slowly to dilute the PEG. The cells are allowed to stand for an additional 1 minute without agitation or mixing. An additional 20 mL of medium A is added over a period of 3 to 5 minutes, and the cells pelleted at 1400 rpm for 5 minutes. The supernatant is aspirated off and the cells resuspended in 20 mL of medium A with 20% fetal calf serum, $1 \times 10^{-4}$ M hypoxanthine, $4 \times 10^{-7}$ M aminopterin and $3 \times 10^{-6}$ M thymidine (medium C or HAT selective medium). Aminopterin is toxic for cells that lack the enzyme HGPRT and therefore kills all unfused myeloma cells. Fused cells (hybridomas) survive in HAT because they obtain HGPRT from the B lymphocyte (spleen cell) fusion partner.

Example 28: Selection of Hybridomas Producing Monoclonal Antibodies

The cell suspension for each of the immunogens prepared above is transferred into a 75 cm2 T-flask and incubated at 37 ° C. in a 5% $CO_2$ incubator for 1–3 hours. The cell suspension is then diluted to $1 \times 10^6$ spleen cells/mL with medium C, and 1 mL volumes of the cell suspensions are added to each well of a 24 well Costar plates. These plates are incubated for 24 hours at 37 ° C. and 5% $CO_2$. After the incubation period 1 mL volumes of feeder cell (non-immunized BALB/c mouse spleen cells) suspension in medium C at 2–3×10$^5$ cells/mL is added to each of the 24 wells of the Costar plates and incubated at 37 ° C, 5% $CO_2$ for 14–17 days. During this period, on alternate days, 1 mL volumes of medium is removed from each well by aspiration and replaced with 1 mL of fresh medium C. On day 10 the supernatants from the hybridoma containing wells are tested for antibody activity. A few hybridoma suspensions are chosen for further cloning by picking those supernatants which demonstrate antibody binding greater than background. For example, binding can be assessed on the TDx analyzer (Abbott Laboratories) using tracers described in examples 16–21. The cells from wells chosen for containing antibody activity are cloned by limiting dilution within 24 hours of sampling.

Example 29: Cloning of Hybridoma Culture that Produces Monoclonal Antibodies.

The cells in antibody secreting wells prepared above are diluted in a volume of medium A and 15% fetal calf serum (medium B) to a concentration of 10 cells/mL and 100 mL of each diluted cell suspension are aliquoted into the wells of three Costar plates of 96 wells each. 100 mL volumes of feeder cells in medium B at 5×10$^5$ cells/mL are added to each well and the plates incubated at 37° C., 5% $CO_2$ for 14 days. Supernatants are again tested for antibody activity using an assay protocol as in the above example. The antibody producing clones are then expanded without feeder cells in 24 well Costar plates and finally in 25 cm2 T-flasks. 32×10$^6$ cells/mL samples of the clone are then stored in medium B with 10% glycerol added, in liquid nitrogen. 1–2 mL samples were then further evaluated for displacement on the TDx instrument protocol and one clone is selected for ascites production.

Example 30: In Vivo Production of Monoclonal Antibodies

An in vivo method for obtaining large amounts of monoclonal antibodies involved the adaptation of method described above to grow as an "ascites" tumor. Female BALB/c mice are "primed" by intraperitoneal injection of 0.5 mL of pristane (2,6,10,14-tetra-methylpentadecane). Pristane is a sterile irritant which elicits a serous secretion ("ascites") in the peritoneal cavity of mice which acts as a growth medium. Approximately 4–5 weeks following the pristane injection, aliquots containing 1.5×10$^6$ actively growing hybridoma cells harvested from in vitro cultures as described in Example 24 are inoculated into the peritoneal cavities of primed mice. Seven days following hybridoma cell injection, 5–10 mL of ascites fluid is harvested from each mouse. Upon purification by ammonium sulfate precipitation approximately 24.6 mg of antibody is obtained per mL of ascites fluid.

Example 31: Fluorescence Polarization Immunoassays

As described previously, the reagents for the FPIA of the present invention comprise tracers and antibodies raised against immunogens of the present invention, specific for tethered intermediates. In addition, conventionally used assay solutions including a dilution buffer, and hapten derivative calibrators and controls are prepared.

The preferred procedure is designed to be used in conjunction with the automated TDx, ADx, or IMx systems; however, manual assays can also be performed. In both procedures, the test sample can be mixed with a pretreatment solution and antibody in dilution buffer before a background reading is taken. The tracer is then added to the test solution. After incubation, a fluorescence polarization reading is taken.

In the automated assays, the fluorescence polarization value of each calibrator, control or test sample is determined and printed on the output tape of the TDx, ADx or IMx instrument. The instrument also generates a standard curve by plotting the polarization of each calibrator versus it's concentration, using a nonlinear regression analysis. The concentration of each control or sample is read off the stored curve and printed on the output tape.

The following reagents are used in the preferred automated hapten derivative assays.

1) the pretreatment solution
2) the tracer diluted in 50% methanol in potassium phosphate buffer (0.15 M phosphate buffer, pH 7.5).
3) the antibody comprising rabbit antisera or mouse monoclonal antibody raised against a hapten derivative immunogen, diluted in TDx buffer (0.1M phosphate buffer, pH 7.5, containing 0.01% bovine gamma globulin and 0.1% sodium azide) with 30% glycerol;
4) a diluent buffer comprising TDx buffer,
5) a sets of calibrators
6) controls comprising 5 mg/mL hapten derivatives All polarized fluorescent measurements are made using the TDx instrument which performed the assay in accordance with the following protocol:

1) 22.5 mL of standard or unknown test sample and 12.5 mL each of the antibody reagent and the pretreatment reagent are delivered into the cuvette and a sufficient volume of diluent buffer is added to raise the volume to 1 mL, and a background intensity reading is taken;
2) 12.5 mL each of pretreatment reagent and antibody, 25 mL of the tracer, and the second 22.5 mL of sample and are added to the cuvette, and a sufficient volume of diluent buffer is added to raise the volume to 2.0 mL;
3) the reaction mixture is incubated;
4) the fluorescence polarization due to tracer binding to the antibody is obtained by subtracting the polarized fluorescence intensities of the background from the final polarized fluorescence intensities of the mixture; and
5) the polarization value for the unknown test sample is compared to a standard curve prepared using calibrators of known hapten derivative content.

What is claimed is:

1. A compound having the following structure:

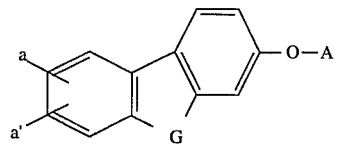

wherein a and a' when taken alone are 1 to 4 groups independently selected from the group consisting of: hydrogen, $C_1$–$C_{10}$-alkyl, $C_1$–$C_{10}$-alkoxy, $C_1$–$C_{10}$-alkylthio, halo-$C_1$–$C_{10}$-alkyl, $C_1$–$C_{10}$-alkylamino, di-($C_1$–$C_{10}$-alkyl)amino, aryl $C_1$–$C_{10}$-alkyl, optionally substituted aryl, halogen, amino, carboxy, carboxamido, hydroxy, mercapto, nitro, nitroso, sulfo, phospho and protected forms thereof; or alternatively a and a' when adjacent and when taken together with the carbons to which they are joined form a fused ring;

G is NR wherein R is hydrogen, $C_1$–$C_{10}$-alkyl, optionally substituted aryl, optionally substituted sulfonyl, thiophenyl, carboxy, carboxamido, and protected forms thereof; and A is a linking moiety of the formula —L—y, wherein y is a functional group selected from phophoramidite and phosphonate and protected forms of these functional groups and L is spacer group consisting of from 1 to about 50 atoms.

2. The compound according to claim 1 wherein a is hydrogen and a' is amino, halogen, hydroxy, nitro, and protected forms thereof.

3. The compound according to claim 1 wherein L is $C_1$–$C_{10}$-alkyl.

4. The compound according to claim 3 wherein a is hydrogen and a' is selected from the group consisting of hydrogen, amino, halogen, hydroxy, nitro, and protected forms thereof.

5. The compound according to claim 1 wherein G is N and R is selected from hydrogen, optionally substituted sulfonyl, and thiophenyl.

* * * * *